US012653449B2

(12) United States Patent
Vera Donoso et al.

(10) Patent No.: US 12,653,449 B2
(45) Date of Patent: Jun. 16, 2026

(54) DEVICE FOR PROSTATE PALPATION

(71) Applicants: IIS La Fe, Valencia (ES); UNIVERSITAT POLITÈCNICA DE VALÈNCIA, Valencia (ES); ASOCIACIÓN INSTITUTO DE BIOMECÁNICA DE VALENCIA, Valencia (ES); CONSEJO SUPERIOR DE INVESTIGACIONES CIENTÍFICAS, Madrid (ES)

(72) Inventors: César David Vera Donoso, Valencia (ES); Francisco de Paula Boronat Tormo, Valencia (ES);

(Continued)

(73) Assignees: UNIVERSITAT POLITÉCNICA DE VALÈNCIA, Valencia (ES); ASOCIACIÓN INSTITUTO DE BIOMECÁNICA DE VALENCIA, Valencia (ES); Fundación Investigación Hospital Univ. y Politécnico La Fe de la Comunidad Valenciana, Valencia (ES); CONSEJO SUPERIOR DE INVESTIGACIONES CIENTÍFICAS, Madrid (ES)

( * ) Notice: Subject to any disclaimer, the term of this patent is extended or adjusted under 35 U.S.C. 154(b) by 319 days.

(21) Appl. No.: 18/546,446

(22) PCT Filed: Feb. 14, 2022

(86) PCT No.: PCT/ES2022/070074
§ 371 (c)(1),
(2) Date: Aug. 15, 2023

(87) PCT Pub. No.: WO2022/171924
PCT Pub. Date: Aug. 18, 2022

(65) Prior Publication Data
US 2024/0130665 A1    Apr. 25, 2024
US 2024/0225526 A9    Jul. 11, 2024

(30) Foreign Application Priority Data
Feb. 15, 2021    (ES) ................................... 202130115

(51) Int. Cl.
A61B 5/00    (2006.01)
A61B 5/06    (2006.01)

(52) U.S. Cl.
CPC .......... *A61B 5/4381* (2013.01); *A61B 5/0053* (2013.01); *A61B 5/066* (2013.01)

(58) Field of Classification Search
None
See application file for complete search history.

(56) References Cited

U.S. PATENT DOCUMENTS 5,265,612 A * 11/1993 Sarvazyan ............. A61B 5/036
600/471
6,142,959 A    11/2000 Sarvazyan et al.
(Continued)

FOREIGN PATENT DOCUMENTS

TW                 I403303 B    8/2013
WO    WO-2021161233 A1 *    8/2021    ........... A61B 5/6853

OTHER PUBLICATIONS

European Patent Office, Written Opinion of the International Searching Authority, International Application No. PCT/ES2022/070074.
(Continued)

*Primary Examiner* — Jacqueline Cheng
*Assistant Examiner* — Jairo H Portillo
(74) *Attorney, Agent, or Firm* — Equip LG; Christopher Quan

(57) ABSTRACT

It consists of a system for palpation of the rectal face of the prostate that transforms the information collected into objective, reproducible and useful information. The system makes it possible to identify areas of high rigidity reaching the entire peripheral area, transforming a diagnostic maneuver for prostate cancer into an objective one, which until now has been subjective and unreliable. All this in a short space of time, carried out in a less aggressive and more objective way than rectal examination. The device consists of a manual electronic instrument with a handle (1) and a scanning rod (3), which includes at least two concentric force/pressure sensors of different heights, as well as an ultrasonic imaging system which, through means of connection to (Continued)

external devices for analysis/control, allows the data obtained to be analyzed and the anatomy of the prostate being analyzed to be visualized in real time.

6 Claims, 2 Drawing Sheets

(72)   Inventors: Noé Jimenez Gonzalez, Valencia (ES); Francisco Camarena Femenia, Valencia (ES); Carlos Manuel Atienza Vicente, Valencia (ES); Ramon Moraga Maestre, Valencia (ES)

(56)                    References Cited

U.S. PATENT DOCUMENTS

| | | |
|---|---|---|
| 6,511,427 B1 | 1/2003 | Sliwa, Jr. et al. |
| 6,569,108 B2 | 5/2003 | Sarvazyan et al. |
| 7,819,824 B2 | 10/2010 | Sarvazyan et al. |
| 8,016,777 B1 | 9/2011 | Egorov et al. |
| 2007/0293792 A1 | 12/2007 | Sliwa |
| 2011/0144541 A1* | 6/2011 | Kuroda ................... A61B 5/224 |
| | | 600/587 |
| 2012/0016238 A1* | 1/2012 | Matsumura .............. A61B 8/12 |
| | | 600/438 |
| 2016/0135728 A1* | 5/2016 | Furukawa ............ A61B 5/6843 |
| | | 600/300 |
| 2018/0000348 A1* | 1/2018 | Bishara ................ A61B 5/6806 |
| 2019/0072671 A1* | 3/2019 | Nikolov ............. G01S 15/8993 |

OTHER PUBLICATIONS

Li Chenggang et al: "Tactile sensor with an inverted V-shaped indenter for elastic tissue identification", Intelligent Service Robotics, Springer Berlin Heidelberg, Berlin/Heidelberg, vol. 13, No. 1, Dec. 7, 2019 (Dec. 7, 2019), pp. 113-121, XP037005852, ISSN: 1861-2776, [retrieved on Dec. 7, 2019], DOI: 10.1007/S11370-019-00304-8 *.

* cited by examiner

DEVICE FOR PROSTATE PALPATION

CROSS-REFERENCE TO RELATED APPLICATIONS

This application is a 371-national stage application of Patent Cooperation Treaty international application Ser. No. PCT/ES2022/070074, filed Feb. 14, 2022, entitled "DEVICE FOR PROSTATE PALPATION", which claims the benefit and priority of Spanish Patent Application No. P202130115, filed Feb. 15, 2021, the contents of all of which are hereby incorporated by reference in its their entireties.

OBJECT OF THE INVENTION

The present invention discloses a device for palpation of the prostate as a screening method for prostate cancer. The object of the invention is to provide a device that allows palpation of the rectal face of the prostate, identifying areas of high rigidity and the limits of the gland, with the aim of detecting prostate cancer.

To characterize prostate stiffness (e.g. stiffness determined by the deformation of the fat layer and stiffness determined by the overall soft tissue layer), the device is configured to measure force and deformation at points on the rectal face of the prostate, by the rectum.

The invention discloses a device and method for performing palpation of the rectal face of the prostate providing an objective and reproducible index for the assessment of tissue stiffness.

Currently, the most common diagnostic maneuver for prostate cancer is the digital rectal examination, which is a manual procedure, making the test subjective and unreliable. In addition, the finger often barely reaches the prostatic apex, resulting in a partial assessment of tissue stiffness.

The methods and devices disclosed in this invention overcome these drawbacks by allowing the identification of areas of high rigidity in a completely objective, less aggressive way, reaching the entire peripheral area, and with a test time similar to that of a digital rectal examination. The device of the invention also has an ultrasonic imaging system that makes it possible to visualize the anatomy of the prostate during the test.

TECHNICAL FIELD

The invention falls within the sector of medical diagnostic device manufacturers, as well as the industry dedicated to the treatment of prostate cancer.

BACKGROUND OF THE INVENTION

The prostate is a gland that lies below the bladder in men and produces the fluid for semen. Cancer screening is a test that is done before you have any symptoms, as cancer that is found early is easier to treat.

The absolute number of cancers diagnosed in Spain and worldwide has continued to rise for decades in probable relation to the increase in life expectancy of the population and is currently the most frequent cancer in men.

In this regard, one of the tests used as a screening method for prostate cancer is the digital rectal examination. In 18% of prostate cancers there is only an abnormal digital rectal examination without an alteration in the blood marker called prostate specific antigen (PSA).

The doctor inserts a gloved and lubricated finger into the rectum to palpate the prostate and, depending on the stiffness of the palpated area, determine a suspected diagnosis.

However, there are a number of problems with this technique:

The first and biggest problem is the lack of objectivity in the analysis of the stiffness of the palpated area, as it is based on the subjective perception of the doctor with respect to the pressure he/she can exert with his/her finger, which can lead to diagnoses that are poorly reliable.

The length of the finger, the dimensions of the patient and the experience of the examiner limit the quality of the examination.

This is a psychologically unpleasant technique for the examiner and the patient. It is therefore desirable to reduce this aspect, which is very uncomfortable and yields little.

In an attempt to obviate this problem, devices for prostate palpation that include a force/pressure sensor are known, as is the case of US 2007293792, which discloses a rectal probe comprising a force/pressure sensor configured to measure prostate rigidity through the rectal wall adjacent to the prostate.

Ideally, the force/pressure sensor is large enough to detect prostate pressure or stiffness and/or prostate tumors. The forces imposed on the sensing device by tumors will typically be greater than those applied by adjacent rectal wall tissues supported by the benign prostate.

In this device the force/pressure sensors are rigidly mounted on the probe to ensure that the force measured by the force sensor corresponds to the applied force.

Due to the physiognomy of the prostate tissues, the application of a pressure/force sensor can give erroneous readings, as it can coincide with small folds so that obtaining different measurements relative to each other is decisive in making a good diagnosis.

On the other hand, these devices do not include means to visualize the anatomy of the prostate, so it is not possible to know precisely the specific area being scanned, and even more so if it is the prostate that is being scanned.

While there are devices that can objectively detect prostate hardening, they are sophisticated ultrasound machines equipped with special probes for shear wave elastography and specific software.

The use of such equipment could be feasible and useful in specialized hospital consultations, but their high cost, large size and limited portability make them unsuitable for initial screening of patients in primary care, where patients first come. In this context, doctors with little training in digital rectal examination have to decide whether a given patient has the conditions to justify a urological consultation, which can lead to false negatives, resulting in complications of the pathology due to late identification or false positives that collapse specialty consultations and generate long waiting lists.

A similar situation is found in other devices of this type such as those disclosed in U.S. Pat. Nos. 6,511,427, 8,016, 777 or US 2002143275.

In short, it can be concluded that to date there is no system for palpation of the rectal face of the prostate that transforms the information collected with the device itself into objective, reproducible and useful information, all in a device that is easy to use and low cost.

DESCRIPTION OF THE INVENTION

The device for prostate palpation disclosed solves the above-mentioned problem in a fully satisfactory manner, allowing palpation of the rectal face of the prostate, identifying areas of high rigidity in the peripheral zone of the gland, with the aim of detecting indurations suggestive of prostate cancer.

For this purpose, the device of the invention takes the form of a hand-held electronic instrument, provided with a handle for its handling joined to a transrectal scanning rod.

The control electronics are integrated in the handle, via the corresponding push button, as well as a series of indicators that show the results of the measurements obtained.

The scanning rod has two concentric indenters near its distal end with different heights, the central one being higher than the external or perimeter one, by means of which pressure is applied to the scanning point, and which are linked to respective internal pressure sensors by means of a lever (external indenter) and a cylinder (internal indenter).

These elements make it possible to measure in vivo synchronized force and deformation at defined points of the prostate through the rectum.

In accordance with another feature of the invention, the device incorporates an ultrasonic imaging system that allows to locate and visualize the anatomy of the prostate, as well as the correct positioning of the pressure sensors.

The ultrasonic imaging system is based on the use of a phased array of at least 8 piezoelectric emitter/receiver elements and a center frequency greater than 2 MHz, with at least 50% bandwidth, with transverse focusing so that a sectoral slice of the prostate can be observed.

The arrangement of the transrectal ultrasound imaging system's emitting elements, preferably curved to fit the cylindrical shape of the stem and to come into contact with the tissue, as well as the size and number of them and the separation distance between them, is optimized so as not to interfere with the correct arrangement of the pressure sensor line, to obtain the best image resolution and the greatest aperture and depth of field.

The transrectal ultrasound imaging system has electronics associated with a wireless communications module or a wired communications interface that allows it to be used with a computer, tablet, smartphone, or other computing device that allows the visualization of ultrasound information. This transrectal ultrasound imaging system provides a visual reference of the prostate to the medical staff performing the examination in real time.

The simultaneous performance of transrectal ultrasound makes it possible to rule out the false positives that can be caused by frequent prostatic calcifications, which would otherwise be associated with areas of elevated rigidity.

Alternatively, the ultrasonic imaging system may be composed of a two-dimensional arrangement of the emitting elements for electronic anatomical image addressing or a one-dimensional arrangement that allows mechanical rotation from the handle for mechanical and low-cost anatomical sectorial image addressing. In this way, the stiffness sensor and probe may not be aligned with the transrectal ultrasound image, in order to obtain images of different prostate slices from the same position of the stiffness sensor and to improve scanning and rule out false positives.

Alternatively, the ultrasonic imaging system may be located at a position inside the stem such that the ultrasonic image includes the area of the pressure sensor and the tissue in contact with it. In that case the inside of the stem will include a medium with an elasticity and density that allows for proper ultrasound propagation using an acoustic impedance matching layer. This provision provides additional information about the quality of the contact between the pressure sensor and the tissue, which is used to ensure correct physical contact between the sensor and the tissue.

In addition, this configuration allows correlation of echogenic information with information from pressure sensors.

Alternatively, there may be a dedicated ultrasonic imaging system for quality control of the coupling between the pressure sensor and the tissue.

In this way, the device will be introduced through the anus of the patient to be explored by means of its exploration stem so that the rectal side of the prostate will be mapped through it in order to detect indurated areas that suggest prostate cancer.

Optionally, the number of sensors could be increased, in order to simplify the use of the device by simultaneously palpation a larger surface area.

Based on this structure, a system of palpation of the rectal face of the prostate is achieved that transforms the information collected with the device into objective, reproducible and useful information, making it possible to identify areas of high rigidity by reaching the entire peripheral area when, currently, on many occasions the finger barely reaches the prostatic apex during the manual procedure, and transforming a diagnostic maneuver for prostate cancer that until now has been subjective and unreliable into an objective maneuver. All this in a short space of time, performed in a less aggressive and more objective manner than digital rectal examination.

In addition, the health care operator performing the examination must avoid contact between the bowel wall and the indenters during the insertion and removal of the device in the rectum.

For this purpose, the device can incorporate two alternative systems to facilitate the maneuver:
1. A sheath that covers the indenters and that is removed once the area to be assessed has been reached; or
2. A retraction system, internal to the stem, which retracts the indenters into the body of the stem during insertion and allows the indenters to be extracted when the area to be assessed has been reached, by means of a control system in the handle.

DESCRIPTION OF THE DRAWINGS

In order to complement the description to be given below and in order to help a better understanding of the features of the invention, in accordance with a preferential example of practical implementation of the same, a set of drawings is attached as an integral part of this description, in which the following is illustrated for illustrative purposes and without limitation.

PREFERRED EMBODIMENT OF THE INVENTION

In view of the figures shown above, it can be seen that the device for prostate palpation disclosed consists of a handheld electronic instrument, equipped with a handle (1) for its operation, and a probe (3).

Figure 2:
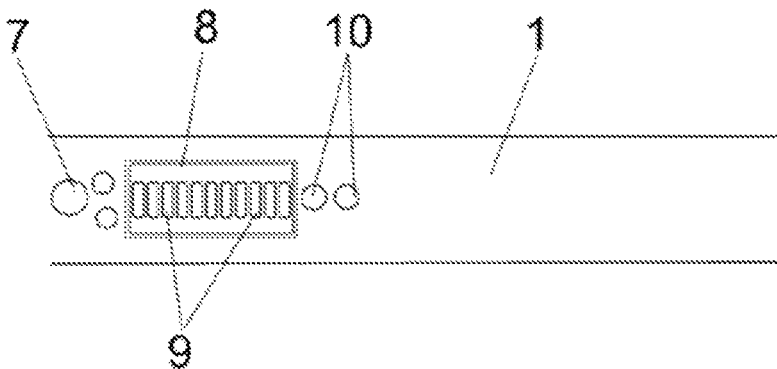
FIG. 2 shows an enlarged detail of the control interface located on the handle of the device.

More specifically, the control electronics are integrated in the handle, with a cover (2) for access to it, so that it has a pushbutton (7) for managing the device (on or off; activation or deletion of readings), as well as a scale (8) on which the different pressure levels (9) are displayed, and may include indicator lights (10) to show the measurement results, the power on of the equipment or the state of charge of the battery, all as can be seen in FIG. 2.

Figure 1:
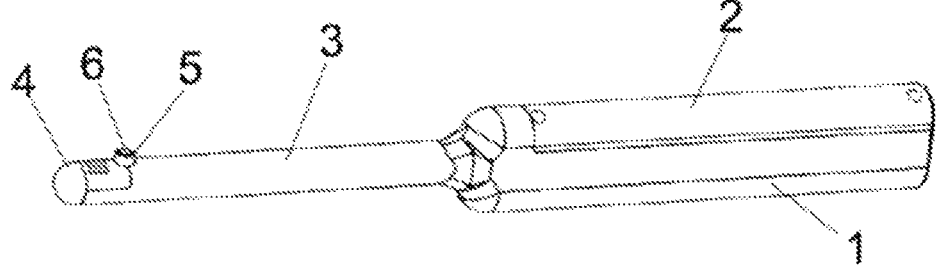
FIG. 1 shows a perspective view of a device for prostate palpation made in accordance with the object of the present invention.

Returning again to FIG. 1, in proximity to its distal end (4) of the scanning rod (3) there are two concentric indenters (5-6) of different heights, the central one being higher than the external or perimeter one, the latter having a diameter of about 5 millimeters, The latter having a diameter of around 5 millimeters, elements by means of which pressure is applied to the exploration point, and which are linked to the respective internal pressure/force sensors by means of a lever (external indenter) and a cylinder (internal indenter).

In order to be able to visualize the anatomy of the prostate, as well as the exact point on which the device is positioned when taking measurements, the device is intended to include an ultrasonic imaging system, based on the use of a "phased array" or phase emitters, i.e. a set of emitters in which the relative phases of the signals fed to each emitter are intentionally varied in order to alter the radiation pattern of the set, involving at least 8 elements with a central frequency of at least 2 MHz, allowing the visualization of a sectorial section of the prostate, electronics associated with a wireless communications module or cable connection that allows it to be used with a computer, tablet, smartphone or other computer device that allows the visualization of the ultrasound information.

Figure 3:
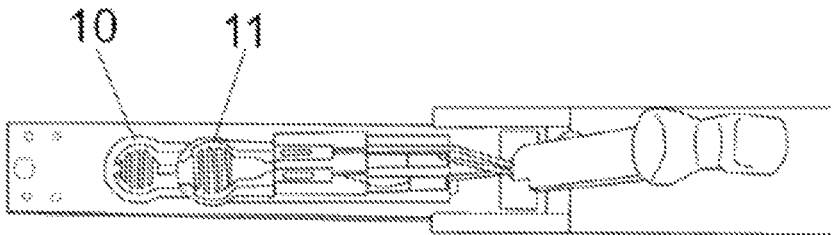
FIG. 3 shows the position of the pressure sensors, located in the mechanical assembly formed by the support base and the hinged lever at the end of the base (raised in the figure). The left sensor (10 in the figure) receives the force from the inner indenter directly; the inner sensor (11 in the figure) receives the force from the outer indenter indirectly, through the central support of the lever where this second indenter is located.
Figure 4:
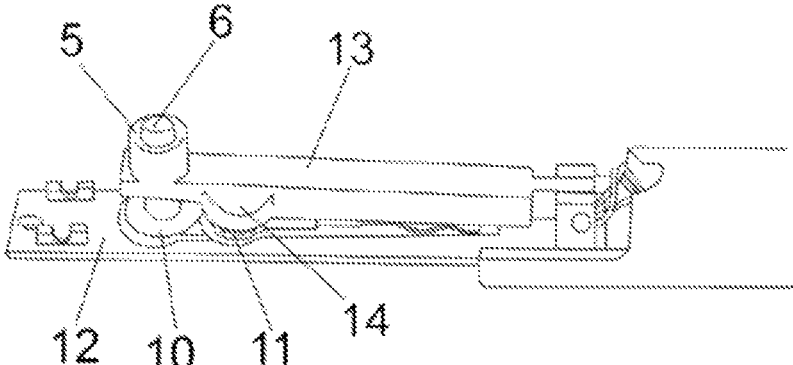
FIG. 4 shows the indenter and sensor base assembly, mounted in its working position, which is inserted into the scanning rod (3) at its distal end and closed by a rounded cap (4). It has a support base for the sensors (12). The outer indenter (5) is integrated in a lever (13), hinged at its end on the base, and transmits the force to the corresponding sensor (11), by means of a central support (14). The inner indenter (6) passes through the inside of the outer indenter (5), being of greater overall height, and transmits the force to the corresponding sensor (10).

As shown in FIGS. 3 and 4, the device makes it possible to simultaneously transmit the force exerted by two indenters (5 and 6) to two sensors (10 and 11), by means of a lever mechanism (13) with central support (11) and external indenter (5), and with concentric internal cylindrical indenter (6).

In addition, as indicated above, the health care operator performing the examination must avoid contact between the bowel wall and the indenters during the insertion and removal of the device in the rectum.

For this purpose, the device can incorporate two alternative systems to facilitate the maneuver:

1. A sheath that covers the indenter and that is removed once the area to be assessed has been reached; or
2. A retraction system, internal to the stem, which retracts the indenter into the stem body during insertion and allows it to be extracted when the area to be assessed has been reached, by means of a control system in the handle.

Finally, it only remains to note that, as mentioned above, the number of pressure sensors could optionally be increased in order to simplify the use of the device by simultaneously palpation a larger surface area.

The invention claimed is:

1. A device for prostate palpation, comprising:
a handle for handling of said device; and
a probe comprising:
(a) concentric inner and an external indenters of different heights adapted to apply pressure to a scanning point, said indenters inserted into and positioned proximally to a distal end of a scanning rod, said inner indenter passing inside of and being higher than said external indenter, said inner indenter being linked to a left internal pressure sensor by a cylinder and said external indenter being linked to an inner internal pressure sensor by a lever which is integrated with said external indenter, wherein said left internal pressure sensor receives a first force directly from said inner indenter, said inner internal pressure sensor receives a second force from said external indenter indirectly by means of a central support, and wherein said concentric inner and external indenters, and said inner and left internal pressure sensors are closed into said distal end of said scanning rod by a cap;
(b) an ultrasonic imaging system located inside said scanning rod that allows visualization of location of said left and inner internal pressure sensors and prostate anatomy for correct positioning of said left and internal pressure sensors in and adjacent to a cancerous area so that measurements are valid; and
(c) control electronics integrated with said handle for left and inner internal pressure sensors and said ultrasonic imaging system with means of connection to external devices for analysis and/or control.

2. The device for prostate palpation according to claim 1, wherein said handle comprises a push button for activating reading of said left and inner internal pressure sensors of said device, a scale for displaying different pressure levels, and indicator lights.

3. The device for prostate palpation according to claim 1, wherein said ultrasonic imaging system is embodied in a set of transmitters/receivers with different relative phases, involving at least 8 elements with a central frequency of at least 2 MHz, bandwidth of at least 50%, which focuses in such a way that a sectorial section of a prostate can be observed, and electronics associated with a wireless communications module or USB connection with a computer, a tablet, a smartphone or other computer device that allows visualization of ultrasound information.

4. The device for prostate palpation according to claim 1, comprising several pairs of pressure/force sensors.

5. The device for prostate palpation according to claim 1, comprising a sheath covering said inner and external indenters.

6. The device for prostate palpation according to claim 1, comprising a retraction system internal to said scanning rod.

* * * * *